United States Patent [19]

Stoppini et al.

[11] Patent Number: 5,759,846
[45] Date of Patent: Jun. 2, 1998

[54] DEVICE FOR THE STUDY OF ORGANOTYPIC CULTURES AND ITS USES IN ELECTROPHYSIOLOGY AND BIOCHEMISTRY

[75] Inventors: Luc Stoppini, Geneve, Switzerland; Philippe Correges, Lugrin, France

[73] Assignee: Chemodyne S.A., Switzerland

[21] Appl. No.: 765,043

[22] PCT Filed: Apr. 10, 1996

[86] PCT No.: PCT/IB96/00300
§ 371 Date: Dec. 10, 1996
§ 102(e) Date: Dec. 10, 1996

[87] PCT Pub. No.: WO96/32467
PCT Pub. Date: Oct. 17, 1996

[30] Foreign Application Priority Data

Apr. 12, 1995 [FR] France ................... 95 04410

[51] Int. Cl.[6] ................... C12M 3/00
[52] U.S. Cl. ................... 435/284.1; 435/287.1; 435/288.3; 435/297.2; 422/82.01; 422/104
[58] Field of Search ................... 422/82.01, 104; 435/29, 284.1, 287.1, 288.3, 297.2

[56] References Cited

U.S. PATENT DOCUMENTS

| | | | |
|---|---|---|---|
| 4,889,691 | 12/1989 | Argentieri | 422/102 |
| 5,064,618 | 11/1991 | Baker et al. | 422/82.01 |
| 5,126,034 | 6/1992 | Carter et al. | 204/403 |

FOREIGN PATENT DOCUMENTS 0 609 458  8/1994  European Pat. Off.

OTHER PUBLICATIONS

Keese et al., I.E.E.E. Eng. Med. Biol. 13(3), 402–408 (1994).

*Primary Examiner*—Kenneth R. Horlick
*Attorney, Agent, or Firm*—Bierman, Muserlian and Lucas

[57] ABSTRACT

Device for studying and recording the electrophysiological phenomena in cultures of excitable tissues, said device comprising a combination of a lower half card comprising a perfusion medium in a perfusion chamber sealed by a permeable and transparent membrane and an upper half card with a flexible printed circuit bearing a network of electrodes and fitted with a cap for insuring the closure of the device and a method of use thereof.

18 Claims, 12 Drawing Sheets

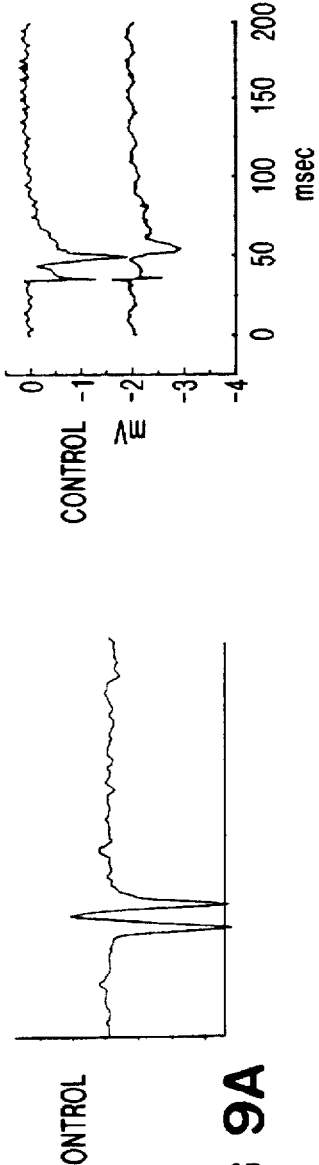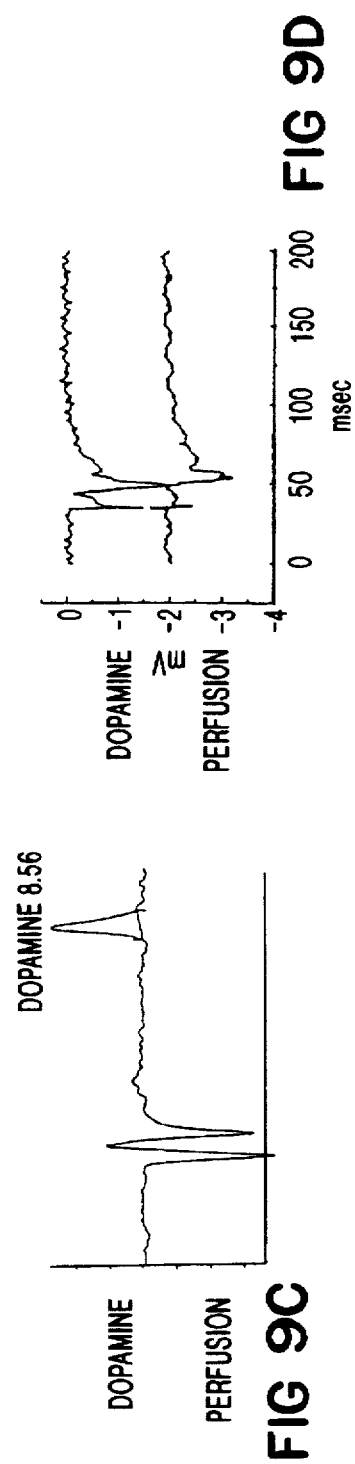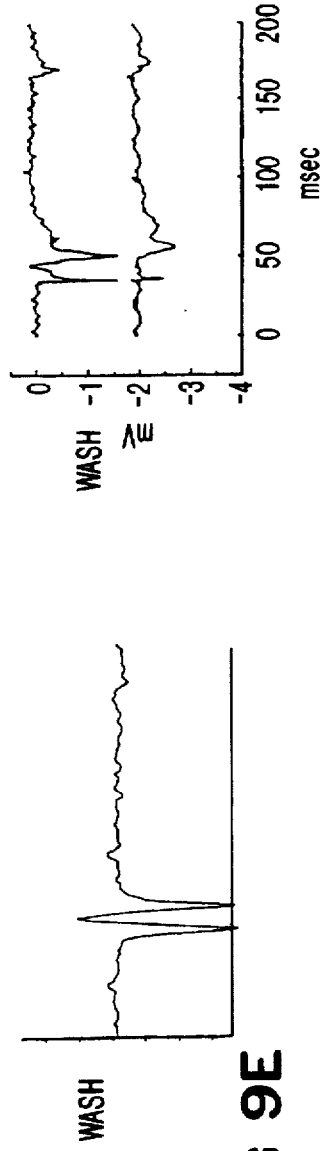

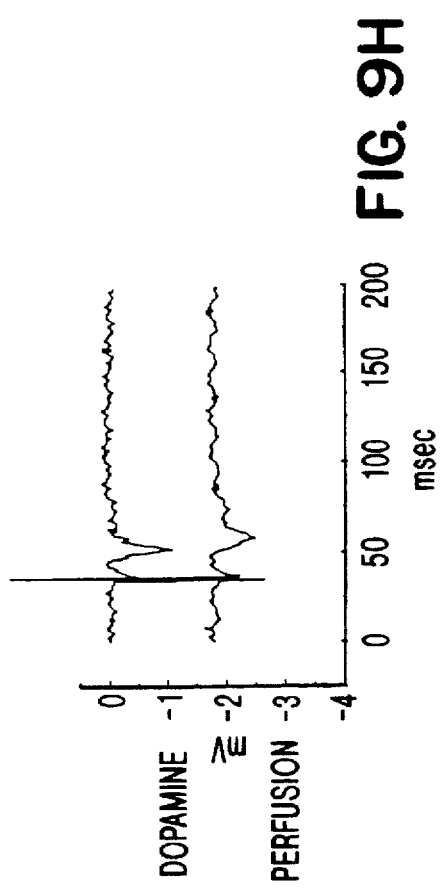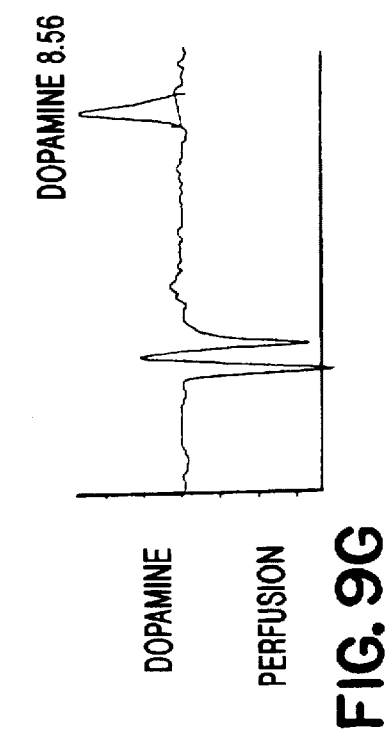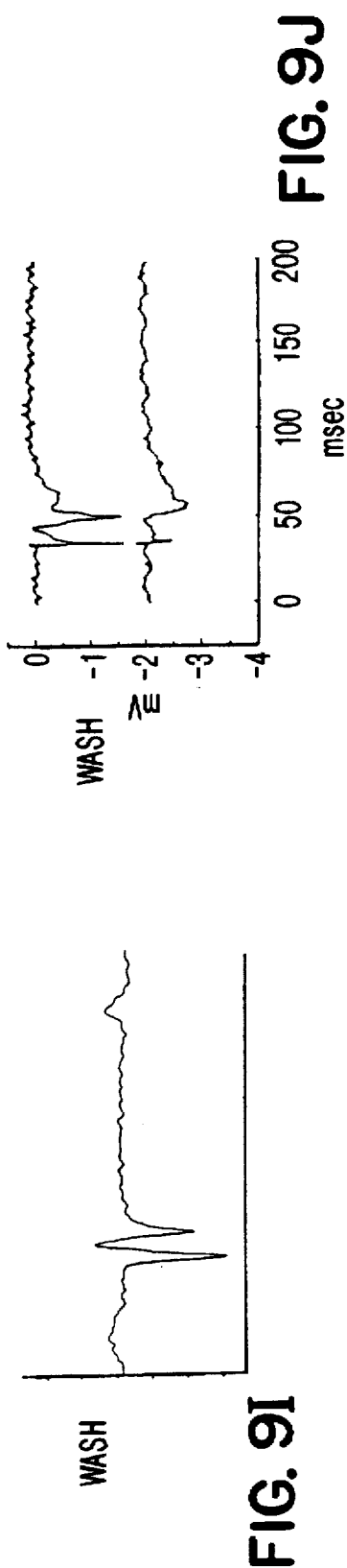
FIG. 9G  FIG. 9H  FIG. 9I  FIG. 9J

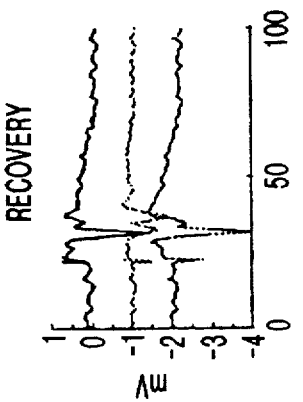
FIG. IIA
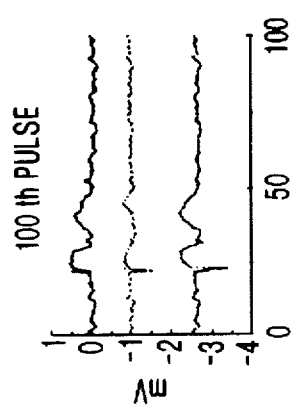
FIG. IIB
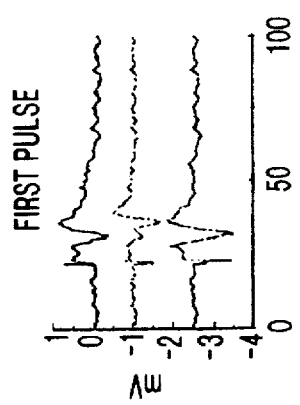
FIG. IIC
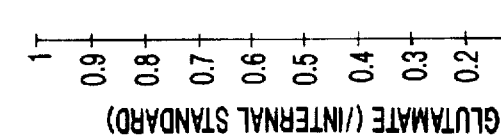
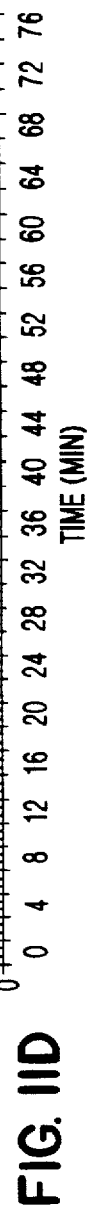
FIG. IID

DEVICE FOR THE STUDY OF ORGANOTYPIC CULTURES AND ITS USES IN ELECTROPHYSIOLOGY AND BIOCHEMISTRY

SUMMARY

The present invention relates to the domain of electrophysiology and biochemistry and to the measuring devices in these domains.

The present invention relates to a new device which enables tissular explants or organotypic cultures to be kept alive, allowing the electrophysiological and biochemical activity of the tissue studied to be continuously measured and analyzed.

The invention relates more particularly to the manufacture of an interface between the biological tissue and a suitable electronic module. The complete system allows the study of the electrical phenomena which are produced in excitable tissue cultures and in particular in central nervous tissues during the culture, the regeneration or the differentiation of cells.

Subject matter of the biological/electronic interface is a study device. It is constituted by two half-cards forming the upper part and the lower part respectively of the interface.

A permeable and transparent membrane is fixed on to the lower part of the device. One or several slice cultures rest on it which can be continuously or discontinuously perfused with a liquid nutrient.

PRIOR ART

Various extracellular recordings of the electrophysiological activity have been previously performed using micro electrode arrays. Most of the technologies used were microphotolithography on different types of material, like silicon (Kovacs et al., 1992; Curtis et al., 1992), glass (Thomas et al., 1972; Pine et al., 1980; Novak et al., 1988; Gross et al., 1982 & 1993). From these microelectrode arrays, simultaneous stimulations and recording of neuronal activity were performed on monolayer networks (Gross et al., 1993).

So far, the longest recording periods on nervous slices did not exceed 14 hours. In order to improve the survival conditions of the tissue, perforation of the stand was performed by some authors (Boppart et al., 1992).

Usually two methods were used. The first, is an exterior stimulation and recording by the micro electrode array; the second, is a stimulation by the network and recording by a conventional glass micro pipette. All those systems involved a recording chamber placed in a Faraday cage and most of them needed a classical electrophysiological set-up (antivibration table, head stage, amplifier, stimulation unit, isolation unit, oscilloscope, micro manipulator, . . . ). In most cases the biological material used were dissociated neurones or acute slices. Cells or tissue were laid down onto a planar electrode array and most of the time, glia cells were in between neurons and the recording site, impeding correct recordings (Janossy et al., 1990).

So far, no available system provides the possibility to simultaneously stimulate and get multirecordings of electrophysiological activity on organotypic slice cultures from mammals central nervous system (CNS), outside a Faraday cage during several days.

This prior art may be well illustrated by the following references:

D. S Barth and al.—Brain Research 678 (1995) p. 177-190

S. A Boppart—IEEE Transactions on Biomedical Engineering 39 (1992) p 37-42

P. Connolly and al.—Biosensors and Bioelectronics 5 (1990) p. 223-234

A. S. G. Curtis and al.—Med. and Biol. Eng. and Comput. 30 (1992) CE 33-36

P. Fromherz and al.—Science 252 (1991) p. 1290-1293

G. W. Gross and al.—J. of Neuroscience Methods 50 (1993) p. 131-143

E. Hoffer and al.—Am. J. Physical. 266 (1994) p. H2136-H2145

J. Pine—J. of Neuroscience Methods 2 (1980) p. 19-31

S. Martini and al.—J. of Neuroscience Methods 48 (1993) p. 115-121

J. L. Novak and B-C Wheeler—J. Neuroscience Methods 23 (1988) p. 149-159

V. Janossy and al.—Acta Biologica Hungarica 41 (1990) p. 309-320

G. T. A. Kovacs and al.—IEEE Transactions on biomedical Engineering 39 (9) (1992) p. 893—902

W. G. Regher and al.—J. of Neuroscience Methods 30 (1989) p. 91—106

C. A. Thomas and al.—Exptl. Cell Res. 74 (1972) p.61-66

Most of these references relate to micro-electrode array, using microphotolithography technology.

The two following references may also be cited:

Ch. Reese and I. Giaever IEEE Engineering in Medicine and Biology 13 (1994) no.3 p.402-408 who describes biosensors made of a small gold electrode immersed in a cell culture medium. This sensor is devised to detect changing impedance consecutive to the attachment of the cells and their growth on the gold electrode, but does not allow the recording of activity of excitable cells.

P. Acquint and al. (Clinical Chemistry 40-1994-p. 1895-1809) disclose a silicon chip micromachined analyser. This system uses silicon technology to produce a pH and $CO_2$ detector in biological fluids, but is not appropriate for the cell culture. This device is made to be implanted and not to study the survival or the growth of slices of culture tissue.

None of these systems allows the study of electrophysiological activity of nervous tissue slices. They cannot deliver any electrical stimulation nor collect the electrophysiological responses, evoked or spontaneous, coming from the nervous system.

DISCLOSURE OF THE PRESENT INVENTION

The present invention was made to remedy the above-mentioned limitations. It is an object of the present invention to permit the long term survival of mammals CNS slice cultures in order to study electrophysiological activity and biochemical analysis of cerebral parenchyma. Organotypic slice cultures keep the tissue organization similar to the in-vivo one.

The three dimensional organization of the tissue allows to gain a current density higher than the one which can be recorded with the dissociated culture cells. Detection of synaptic responses can thus be more easily realized by extracellular recording electrodes. In addition, this kind of tissue culture allows longer recording time compared to acute slices studies. This enables to study long-term phenomena, like delayed neuronal death, neurotoxicity or neurodegenerative processes.

With this system one can perform continuous and simultaneous stimulation and recording of neuronal activity during several days. Microdialysis technique was adapted to the electronic/biological interface according to the invention, in order to collect biochemical molecules from the extracellular medium or to deliver chemical molecules into the cerebral parenchyma.

PREFERRED EMBODIMENTS OF THIS INVENTION

The device includes two half-cards which fit together to form one card which can be inserted into an electronic module specially designed for this purpose.

This card can be perfused in a sterile manner either with a control culture medium, or with a selected culture medium containing the substances which one desires to test or the mediators the effects of which on the preparation, one desires to determine. The composition of the culture medium is defined more precisely in the experimental part.

' A method described by L. Stoppini (Journal of Neuroscience Methods 37 (1991) p. 173) was already known, in which slices of nervous tissue from rat hippocampus were kept under culture at the interface between the air and a culture medium. The slices, placed on a sterile, transparent and porous membrane, were kept in a Petri dish placed in an incubator. Histological and electrophysiological studies made it possible to show that this technique allowed explants to be kept alive and a tissular organization close to that which can be found <in vivo>, to be retained.

The aim of the present invention is to enable organotypic cultures to survive outside an incubator and a Faraday cage and to be able to carry out, on these cultures, continuous electrical stimulations and electrophysiological recordings, over several days up to several weeks.

For this purpose, the device according to the invention allows a network of biocompatible electrodes (plated gold 24 carats) to be put in contact with the surface or with the inside of the tissue studied.

The lower part of the card is made of plastic material and comprises a cavity having an inlet and an outlet. The cavity is delimited by a permeable and transparent membrane. Tissue slices (200–400 μm) produced by a chopper or a Vibratome is placed on the membrane. The culture medium passes through the membrane by capillary and covers the tissue with a film of liquid. This arrangement is effective for ensuring a good survival of the cells for several weeks by supplying the necessary nutriments and facilitating the diffusion of oxygen and carbon dioxide throughout the tissue slices.

The inlet and the outlet for the liquids of the lower part of the card can be sealed by a septum of medical quality, thus forming a lock which enables the contained liquids of the lower chamber, to be preserved. It can then be conveniently replaced in one run or continuously, in a sterile manner, without having to proceed with this operation under a sterile atmosphere or under laminar flow.

The upper part of the card is fixed, using clips, or screw systems to the lower part. The upper part of the card is composed of an element made of plastic material and a flexible printed circuit which forms a network of electrodes attached to connectors.

The plastic element has a well containing a moveable sleeve which can progressively move downwards when a cap is screwed on the well. The downwards progression of the sleeve, by pressing on the flexible printed circuit, allows the electrodes to be vertically positioned on the surface of or inside the slice. By this process, there is no twisting movement exerted on the flexible printed circuit and in this way one avoids damaging the biological tissue.

The presence of a flexible or rigid seal between the two half-cards ensures the impermeability of the gaseous chamber of the upper half-card of the device. This chamber is continuously humidified by evaporation through the membrane of the medium contained in the cavity provided to contain the liquid of the lower half-card. When necessary, a damp filter paper can also be added to a portion of the sleeve.

Observation of the tissue can take place by visual examination, by transparency, both of the upper side and the lower side of the card.

The tissular explants which are placed in the device can be kept alive up to several weeks outside an incubator and are thus monitored, at the same time, by visual supervision and by electrophysiological monitoring.

The tissular explants can be cultured either directly in the card, or can initially be cultivated in an incubator on membrane discs, placed in Petri dishes. The slices of tissue cultivated on the membrane pastilles can then be placed on the membrane of the card. The tissular explants can survive in this way in spite of the overlapping of two membrane layers.

The survival of the tissues studied was revealed by labeling using vital stains on the living tissue and by Histological studies under light-optical, electron microscopy and by immuno-histochemical studies, after fixation of the tissues.

The survival of the tissues studied was in particular revealed after labeling with vital stains and by measuring the lactate dehydrogenase (LDH) content in the culture medium. In addition, immuno-histochemistry provides information about the return to operation of the neurons and of glial cells, bringing about the labeling of the neurofilaments for the neurons and the labeling of the<glial fibrillary acidic protein>(GFAP) for the glial cells.

The electrophysiological recordings allow the immediate determination, as a function of the responses obtained, of the physiological condition of the excitable tissue studied.

Measurement of the activity of the tissue comprises the recording, digitalization and measurement of the spontaneous electrophysiological responses and of the evoked responses.

ELECTRONIC MODULE

The electronic module is composed as follows: the biological/electronic interface card plugs into an electronic module the functions of which are the following: Each electrode of the interface can be dedicated either to positive stimulation (Stim+) or to negative stimulation (Stim−)

to recording (Rec.)

to earth (ground)

Description of these three functions

Stimulation

Stim+, Stim−: the order for stimulation and triggering is given either by the computer, or by an external stimulator. All the stimulation electrodes are electrically isolated by optocoupling. They also have a variable gain and can be permuted.

Recording

After adjustment of the impedance, conversion to AC, amplification by a convenient factor (e.g. 100, 500), and an adjustable offset, the choice of acquisition channels for the analogue/digital conversion card is possible.

Grounding

To avoid a phenomenon of antenna, the non-utilized electrodes are put at the reference potential.

The reference electrode is made by gold deposition around the lower chamber. This electrode is in close contact with the culture medium when it is injected in the lower part chamber. When the two half cards are adjusted, this reference electrode is automatically connected to the electronic ground.

A test for good positioning of the card is visualized through a lightened diode.

Microdialysis analyses

To show the use of the device according to the invention, details will be given hereafter on the biochemical measurements and the adaptation of the microdialysis technique to the device according to the invention.

Alongside the measurement of the electrophysiological activity, biochemical analyses of the extra-cellular medium can be carried out continuously using one or more microdialysis probes.

The microdialysis probe can be positioned at the level of the membrane situated on the lower part of the card, after what the tissue is placed on or under the probe. Another possibility is to fix the probe on the printed circuit. In this case, the vertical positioning of the probe, relative to the tissue, is carried out in the same way as for the electrodes.

The probe is continuously perfused by means of a syringe fitted with an automatic progression piston.

The dialysate collected from the probe is subjected to an analysis either HPLC with automatic injection using an electrical 6-port valve, by capillary electrophoresis or by radioimmunoassays.

The microdialysis probe also allows one or more molecules to be delivered directly into the parenchyma of the tissue and in this way allows the chemical or physiological changes brought about by these substances to be analyzed.

It is therefore observed that the device according to the invention has the following advantages, relative to the existing devices for <in vivo> and <in vitro> studies:

simplification and time saving with regard to changing the medium maintaining the concentration during the perfusion of molecules tested lack of obligation to place the tissue cultures in an incubator possibility of observing the development of the cultures for several days under a microscope or by means of a video camera saving of space and economy of material disposable analysis cards, which can be industrially produced in large amounts (Mass production)

absence of the risk of residual mixing of the molecules tested possibility of using the device for cultures of dissociated cells or for studying <freshly dissected> tissue section reduced risk of contamination continuous (chronic) stimulation and recording, for several days to several weeks, of the electrical activity of the tissue studied the culture can be studied either continuously during several days or discontinuously from time to time, when put back into the incubator in-between two recording periods.

BRIEF DESCRIPTION OF THE DRAWINGS

FIGS. 9 A to J are graphs of simultaneous recording of electrophysiological activity (on the left) and biochemical analysis (on the right).

FIGS. 11A and C are stimultaneous recordings of electrophysiological activity and biochemical analysis with the apparatus of FIG. 10 and FIG. 11D in a graph thereof.

Figure 1:
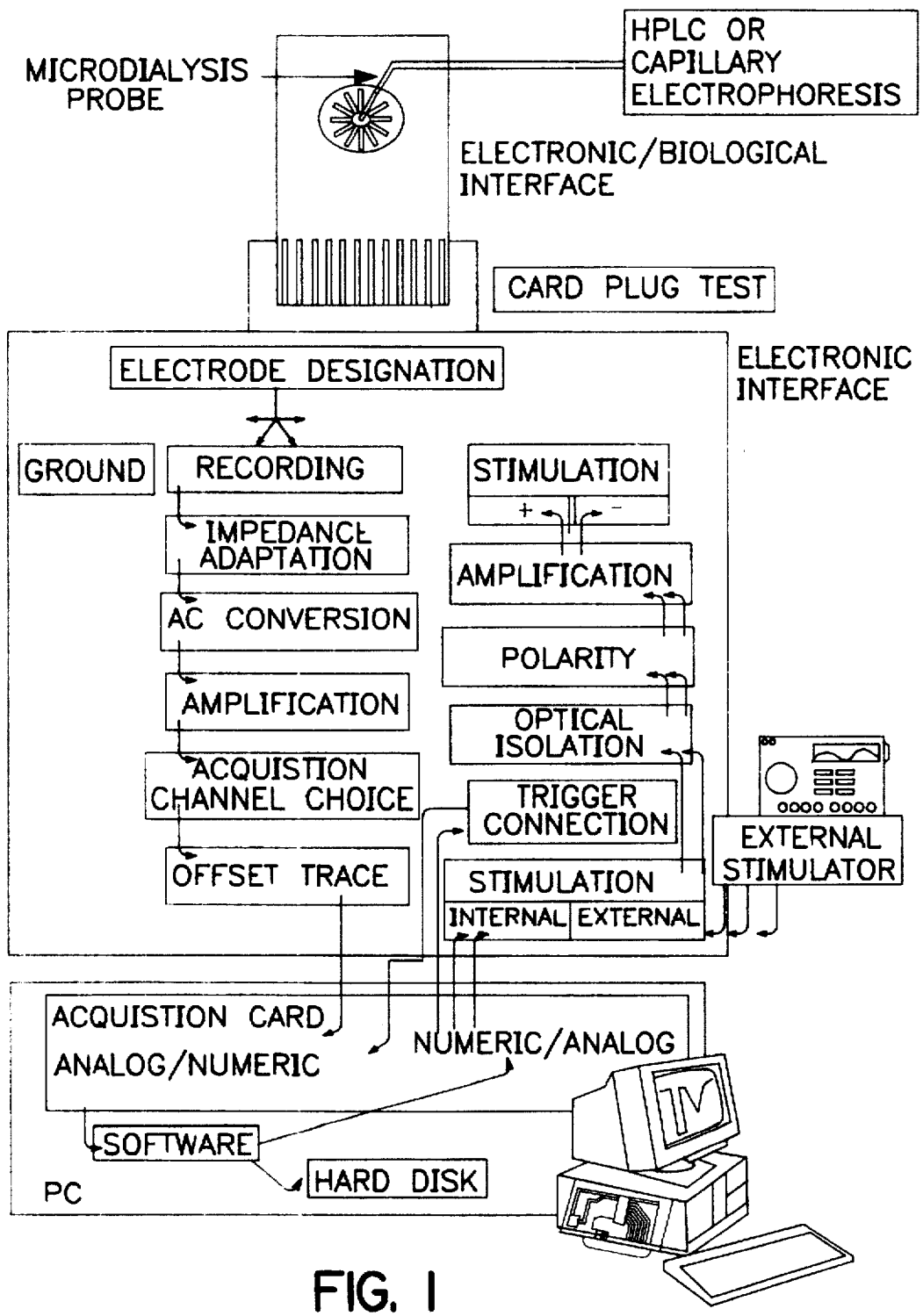
FIG. 1 is a schematic diagram of the system.

The schematic diagram of the system assembly is represented in FIG. 1.

This is composed of three main parts:

A. the biological/electronic interface.

B. the electronic module specially designed to receive the interface to stimulate and to amplify the responses originating from the network of electrodes in contact with the tissue. The interface, can be placed in a thermoregulated chamber and connected to the electronic module by an extension (not shown).

C. a computer which has an acquisition card allowing both the digitalization of the analogic signals and the stimulation and finally, a software which allows the electrophysiological responses to be analyzed.

Figure 2:
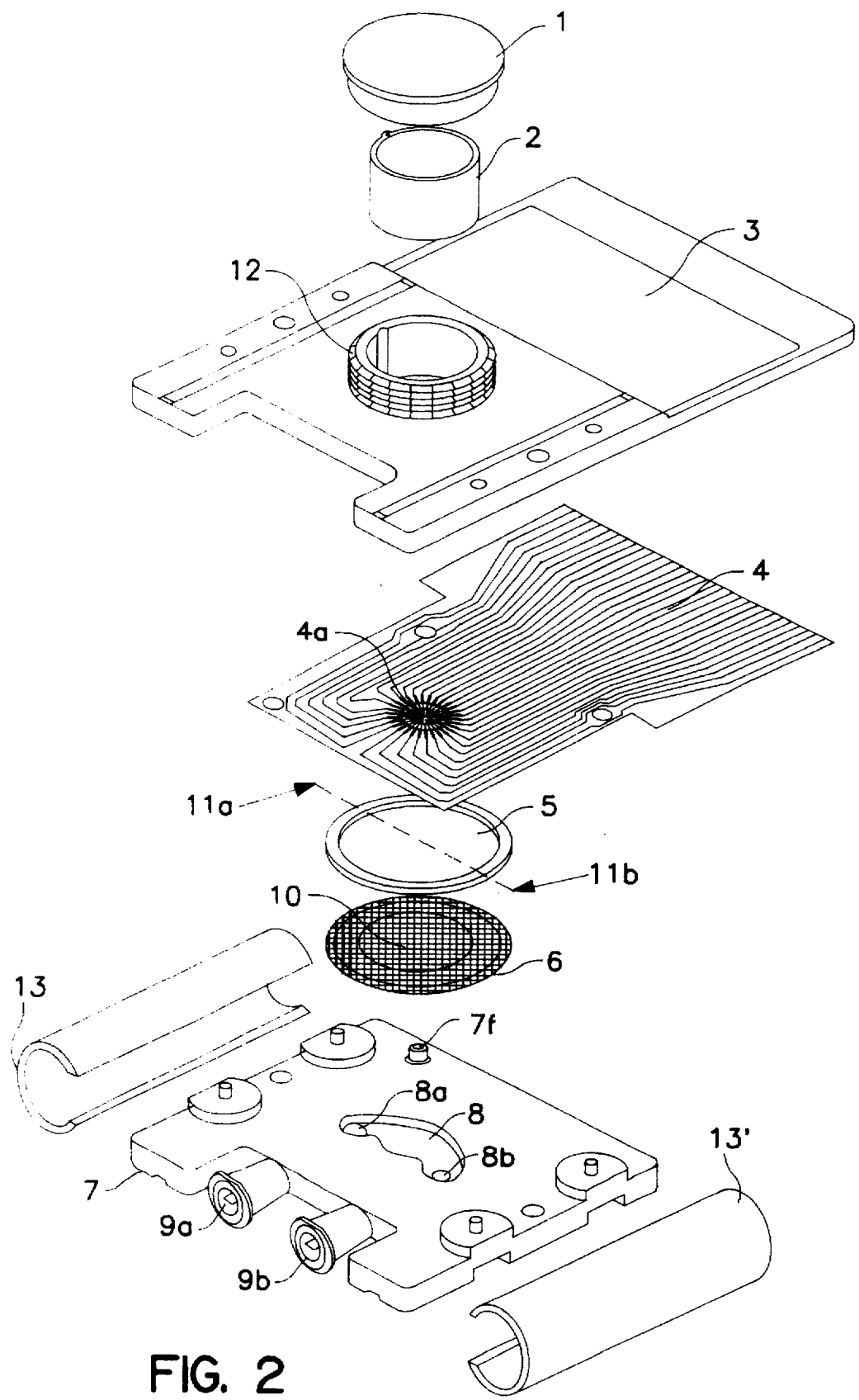
FIG. 2 is an exploded view of the apparatus of the invention.

The schematic diagram of the biological/electronic interface is represented in FIG. 2.

In a preferred implementation, represented in the FIG. 2, the device according to the invention can be defined in the following manner: it comprises two half-cards, the lower one (7) and the upper one (3) which fit together to form the operational arrangement.

The lower half-card has a cavity (8) which contains the liquid culture medium, comprising two supply pipes (8a) and (8b), each forming at its end a lock system (9a) and (9b). The cavity is surmounted by a transparent and permeable membrane (6) on which the tissue sample rests (10). A seal (5) provides air-tightness when the two half-cards (7) and (3) are fitted together. The seal can support one or more microdialysis probes (11a) and (11b) the details of which are provided in FIG. 3.

The upper half-card comprises an outlying well (12) inside which, a sleeve (2) slides. The sleeve can be lowered when the cap ( 1 ) is screwed down.

The two half-cards fit into each other and are fixed together by clips (13) and (13'). The lowering of the sleeve (2) by progressively pressing on the flexible printed circuit (see detail FIG. 4 and 5) (4), moves the gold-plated electrodes (4a) (tags upwards) downwards, which can thus touch the surface of the tissular explant (10). According to the texture of the tissue, a sufficient pressure at the level of the printed circuit (4) will allow the electrodes (4a) to penetrate inside the explant (10), if necessary.

The membrane of the interface can be characterized in the following manner:

the various tests carried out indicate that cultures can survive on membrane whose pore size can vary from 0.02 to 10 μm. The chemical composition of the membrane does not seem to be a determining factor. Membranes of Millicell CM (Millipore), Anopore (Whatman), polycarbonate, PET types give equivalent results.

Characteristics of the flexible printed circuit:
Design: 16 step circuit=76 mm
Materials: Upilex 50 μm+Ci ED 35 μm+Au 0.8 μm
Execution: circuit supplied on a film of 69.975 μm width with S 70 perforation
Tolerances:
  thickness Au 0.2/0.3 μm
  width±75 μm
  image s/perfo±65 μm
  width of the tracks in the window kapton±15 μm Length of flying leads (initially for the transfer automatic bonding technology) can vary from 1.5 to 3.5 mm.

Figure 3A:
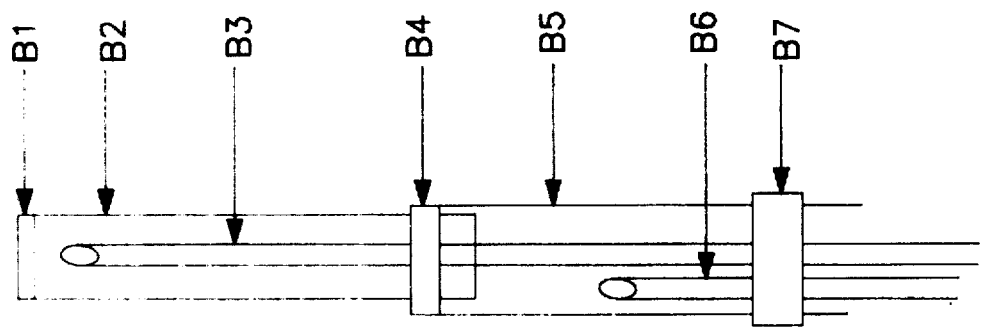
FIG. 3A is a cross section of the microdialysis device.

The schematic diagram of the microdialysis device is represented in FIG. 3.

Figure 3B:
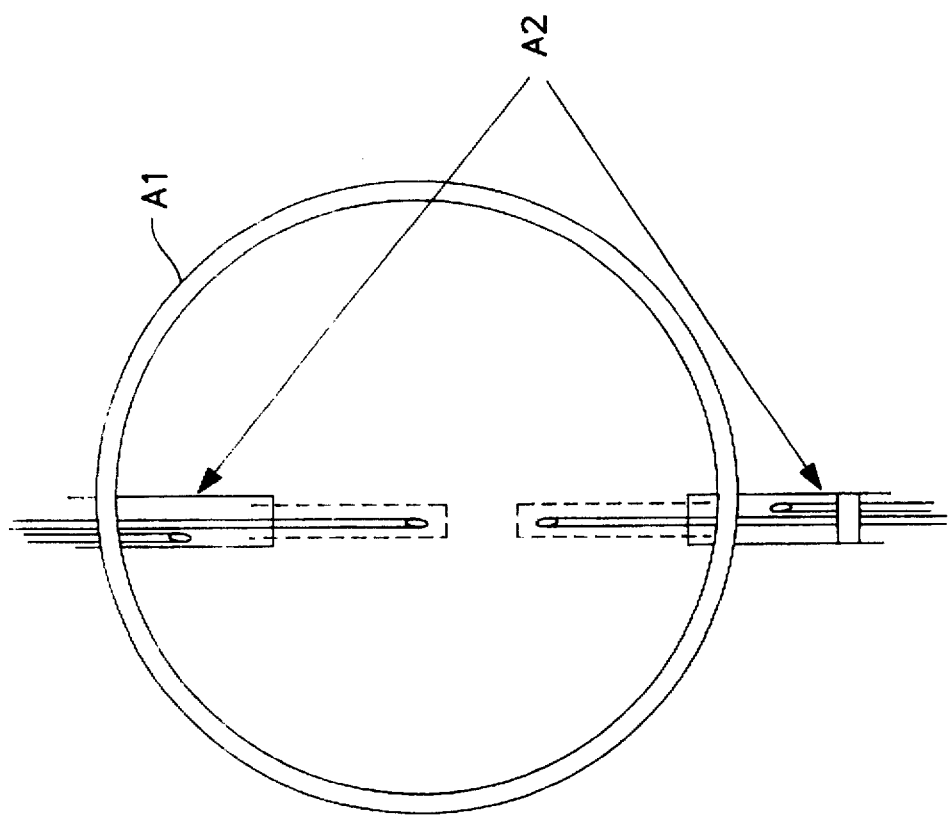
FIG. 3B is a cross section of a probe of the invention.

One or more microdialysis probes (A2) pass through a silicon seal (A1). The detail of one probe is represented in FIG. 3B. A microdialysis bag with a 200 to 300 μm outer diameter (B2) is sealed at its end by a silicon or Epon resin (B1), then inserted into a tube (B5). The impermeability of the connection is produced by a drop of silicon glue (B4 and B7). The dialysis bag is perfused by means of two tubes made of fused silica. The first tube (B3) penetrates as far as the end of the bag and supplies the perfusion solution. The second tube (B6) recovers the dialyzate. The probes are perfused by a physiological solution delivered by means of an automatic syringe-driver. The flow rate of the perfusion is generally comprised between 0.1 and 2 μl/min. The probes can be placed either on the surface of the culture, or be sandwiched between two slices of tissue. The dialysate is directly injected into a pump for HPLC via an electrical 6-port valve with 6 channels, or also can be recovered into flasks ad hoc for subsequent injections.

Figure 4:
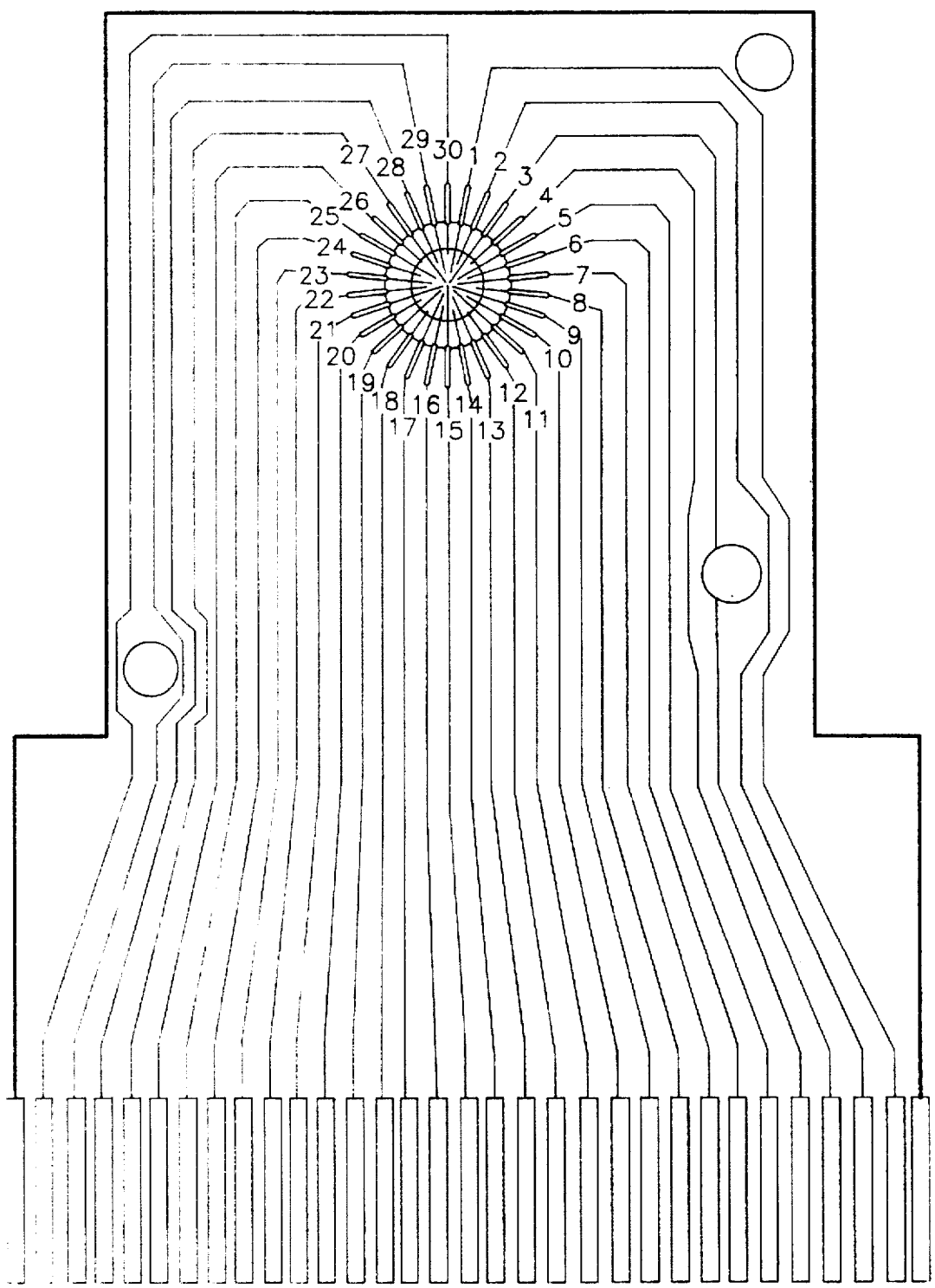
FIGS. 4 and 5 are plan views of the printed circuit.
Figure 5:
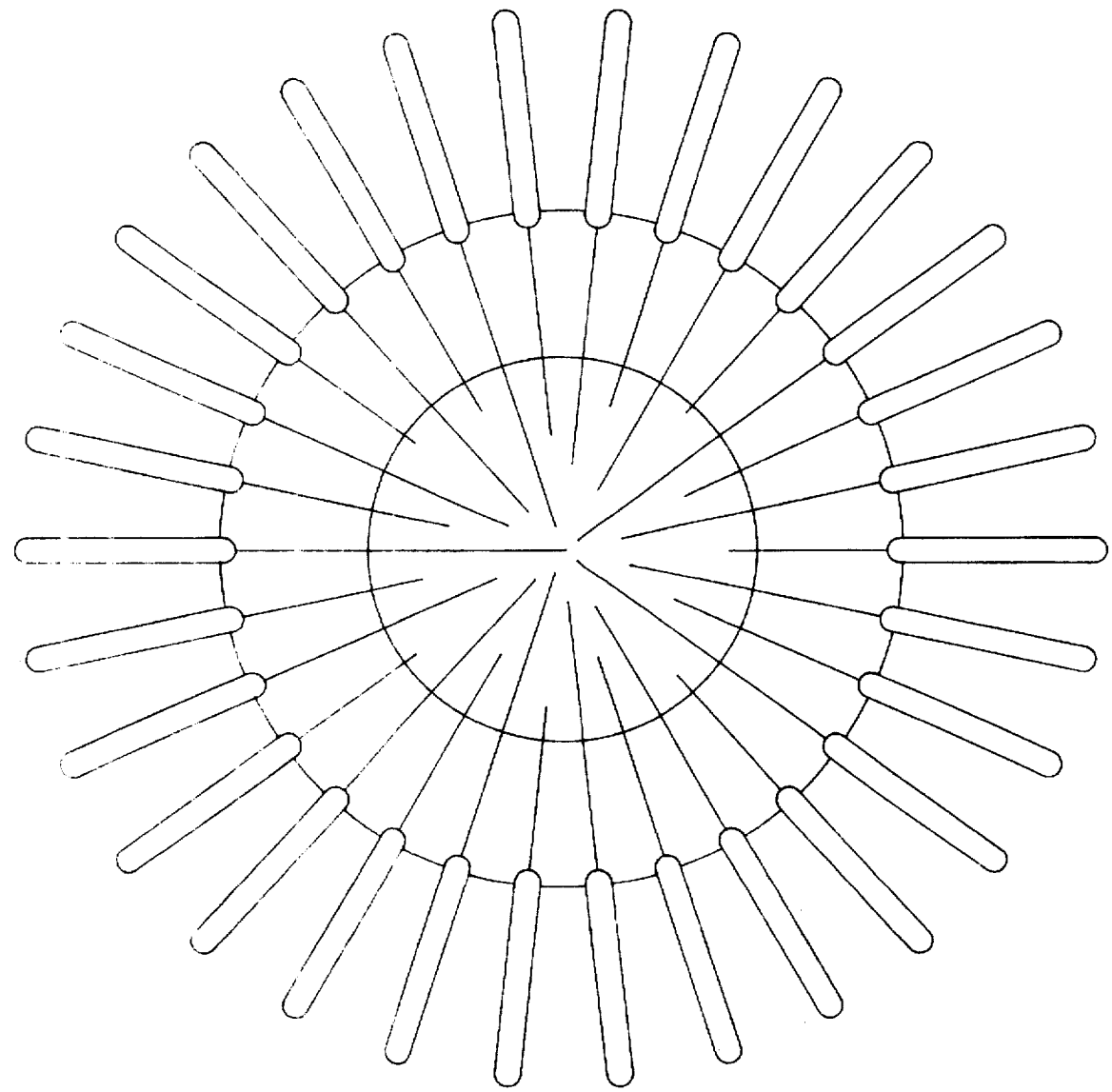

FIG. 4 and 5: details of the printed circuit.

Figure 6:
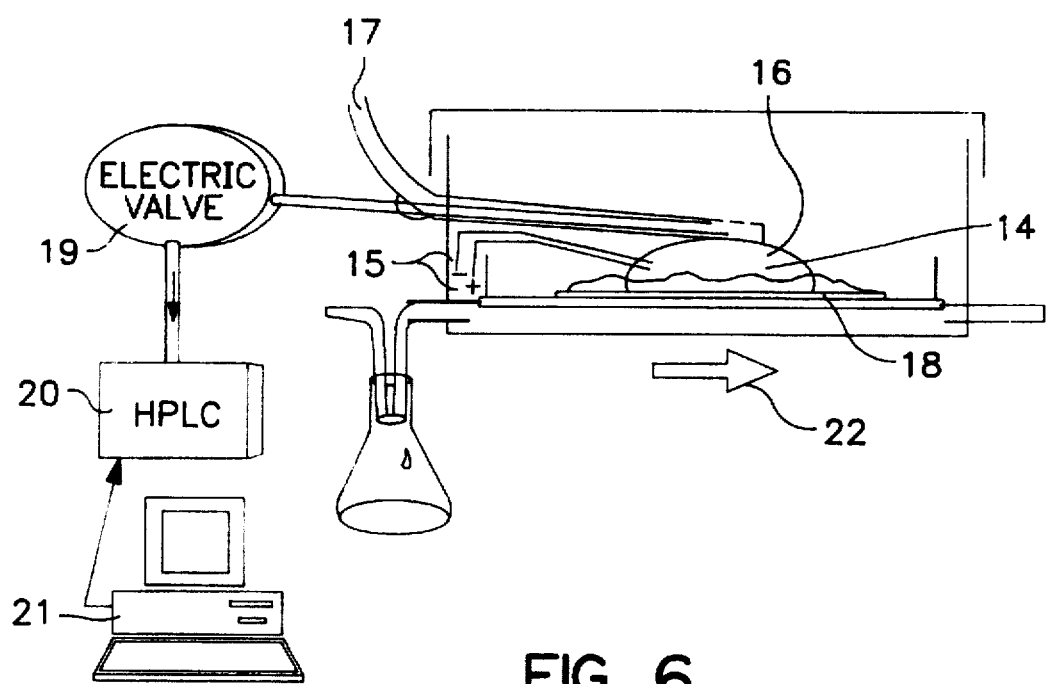
FIG. 6 is a schematic illustration of the system for simultaneous recording of electrophysiological activity and biochemical analysis.
Figure 7B:
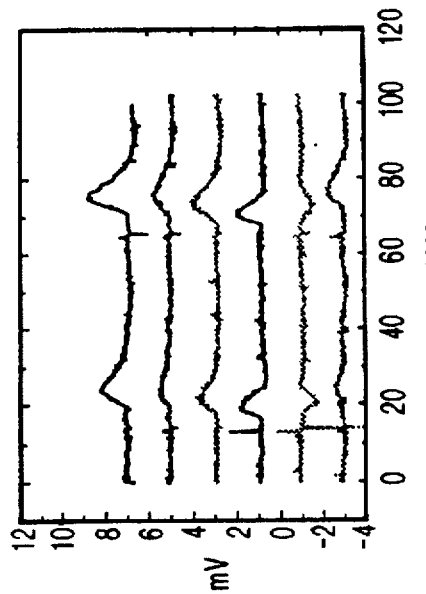
FIG. 7A to D are graphs of responses after a series of pair-pulse stimulation paradigm.
Figure 7D:
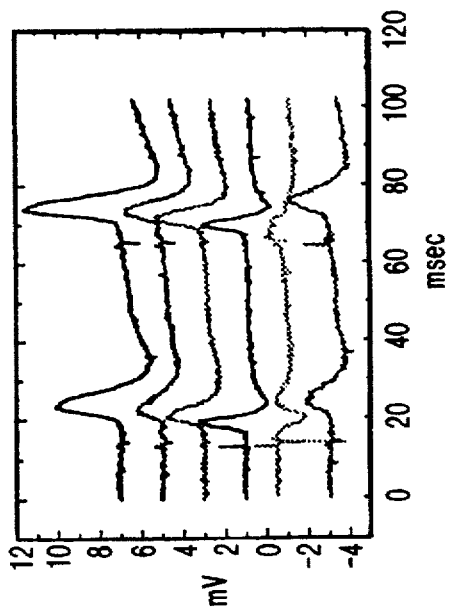
Figure 7A:
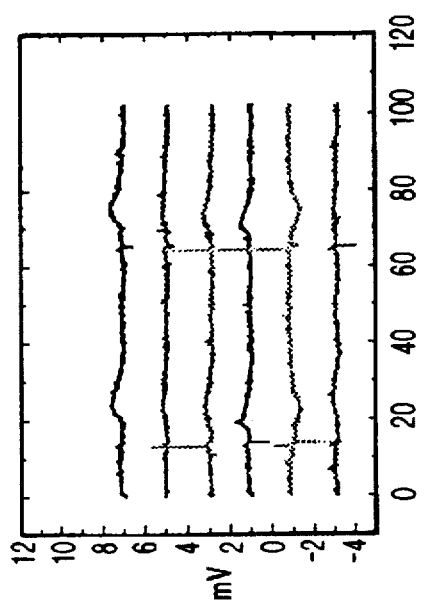
Figure 7C:
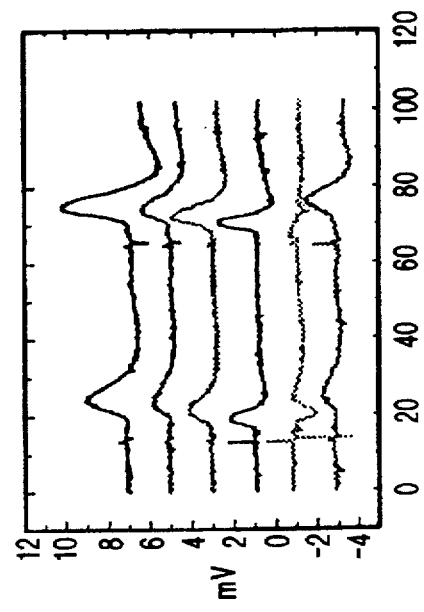
Figure 8B:
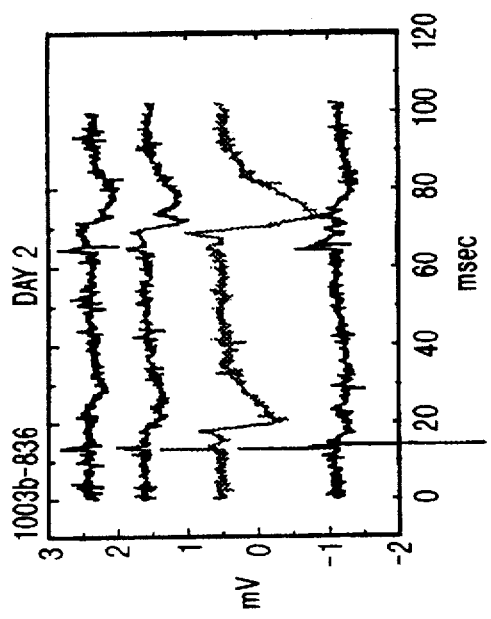
FIGS. 8A to D are graphs of responses obtained after four days of continuous stimulation.
Figure 8D:
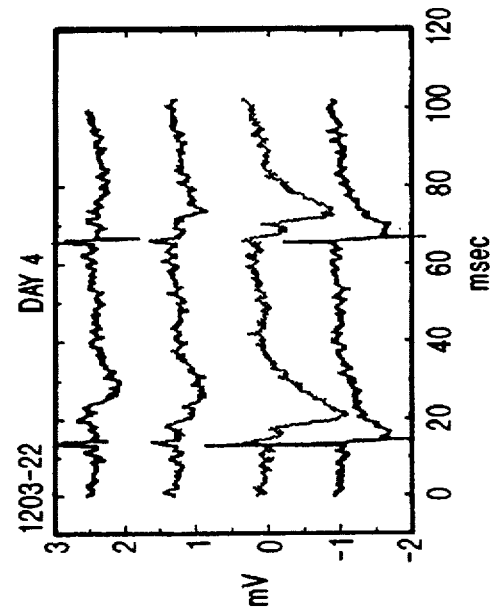
Figure 8A:
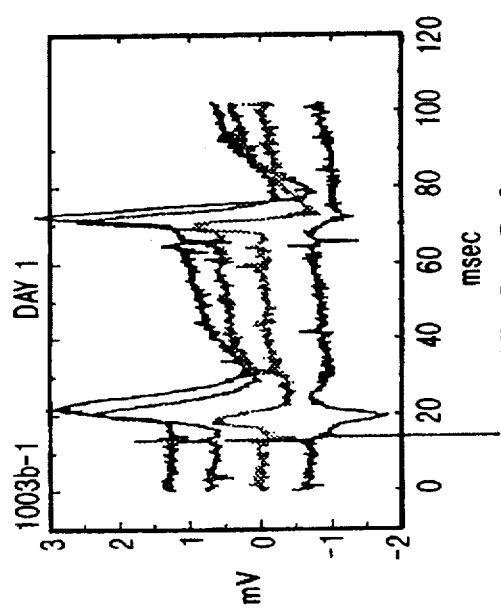
Figure 8C:
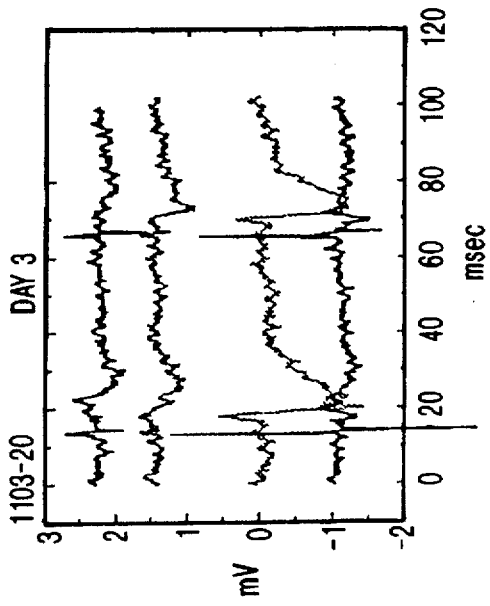

FIG. 6 is a schematic illustration of the system which allows simultaneous recording of electrophysiological activity and biochemical analysis of the microdialysate by an HPLC apparatus (seen in transversal section). Pulses of stimulation can be delivered through stimulating electrodes (15) to the nervous tissue (16) and consecutive evoked responses are recorded by one or several electrodes (14). In addition, molecules released by the tissue or coming from the perfusion chamber (22) through the permeable membrane (18) can be collected by a microdialysis probe (17). Outlet microdialyzates are injected in an HPLC (20) device by an electric valve (19). Chromatographic analyses are performed by a dedicated computer software (21).

FIG. 7 represents examples of evoked responses obtained after a series of pair-pulse stimulation paradigm. Six simultaneous recordings were performed in different hippocampus CA3 and CA1 areas of an organotypic slice culture. Stimulations were applied in the CA3 region.

FIG. 8 shows examples of evoked responses obtained after several days of continuous stimulations (one pair-pulse stimulation every minute). FIG. 8A represents an example of responses recorded during the first day, in FIGS. 8B, 8C and 8D, responses recorded in the following days.

FIG. 9 shows an example of one experiment of simultaneous recording of electrophysiological activity (A,C,E,G,I) and biochemical analysis (B,D,F,H,J) of dopamine diffusion through an hippocampal slice culture. HPLC chromotographs are represented in the left column while concomitant evoked neural activities are illustrated in the right column.

Similarly other mediators can be registered in the same manner such as acetylcholine, noradrenaline, adrenaline and serotonine using similar modes of detection.

Figure 10:
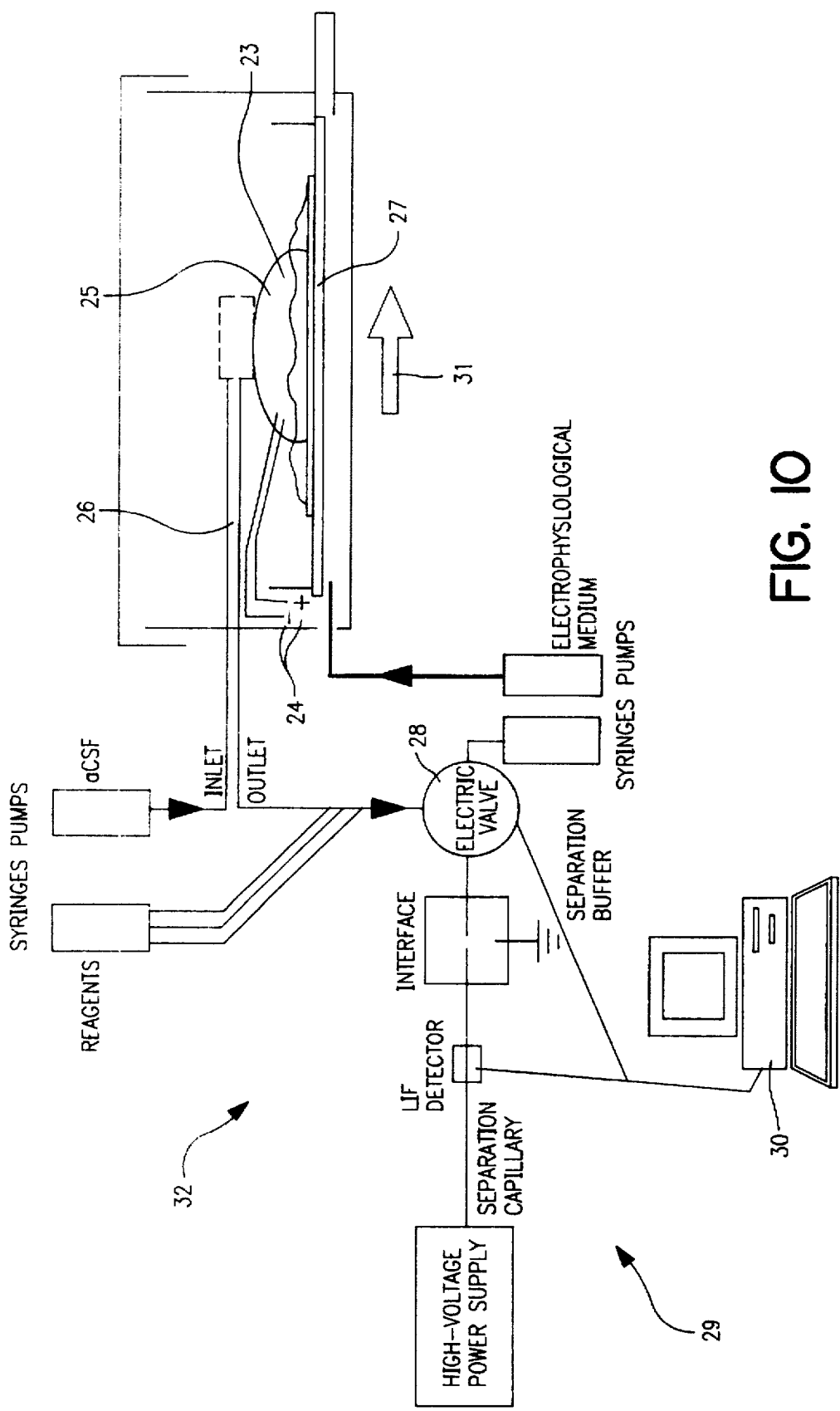
FIG. 10 is a schematic illustration of a a system for simultaneous recording of electrophysiological activity and biochemical analysis using a capillary electrophoresis apparatus.

FIG. 10 represents a schematic illustration of the system (seen in transversal section) which allows the simultaneous recording of the electrophysiological activity and the biochemical analysis of the microdialysate using a capillary electrophoresis apparatus. Pulses of stimulation can be delivered through stimulating electrodes (24) to the nervous tissue (25) and consecutive evoked responses recorded by one or several electrodes (23). In addition, molecules released by the tissue or coming from the perfusion chamber (31) through the permeable membrane (27) can be collected by a microdialysis probe (26). Outlet microdialysates are injected in a capillary electrophoresis device (29) by an electric valve (28). Molecules present in the microdialysate are derivatized (32) and capillary electrophoresis analyses are performed through a CE-LIFD system (29) by a dedicated computer software (30).

FIG. 11 shows an example of an experiment of simultaneous recordings of electrophysiological activity and biochemical analysis of a microdialysate by capillary electrophoresis. A pattern of 100 stimulations was applied to the tissue, the first and the last responses are illustrated in FIG. 11 A and B. FIG. 11 C represents the recovery of electrophysiological response. Results of the time course release of glutamate present in the microdialysate are indicated in FIG. 11D after a stimulation of 3 Hz during 30 sec.

| Chemical composition of the different culture media: | | |
|---|---|---|
| | 100 ml | 200 ml |
| MEM 2× | 25 ml | 50 ml |
| Tris 5 mM | 60 mg | 120 mg |
| Penstrep | 1 ml | 2 ml |
| NaHCO$_3$ | 460 μl | 910 μl |
| Sterile H$_2$O | to 50 ml | to 100 ml |
| Horse serum | 25 ml | 50 ml |
| Hank's medium | 25 ml | 50 ml |

| DISSECTION MEDIUM (medium for culturing): | |
|---|---|
| | 100 ml |
| MEM 2× | 50 ml |
| Penstrep | 1 ml |
| Tris 10 mM | 120 mg |
| Sterile H$_2$O | (completed to 100 ml) |

| DMEM 10% FCS (medium for dissociated cells): | |
|---|---|
| | 100 ml |
| DMEM 2× | 45 ml |
| NaHCO$_4$ | 1.5 ml |
| Penstrep | 1 ml |
| Sterile H$_2$O | (completed to 90 ml) |
| FCS | 10 ml |

| ODM MEDIUM (medium defined without serum) | | |
|---|---|---|
| Complementary medium | | |
| pH 7.26 | | |
| Osm 291 mosm/kg | | |
| CaCl$_2$ | 1 mM | 22 mg |
| KCl | 3 mM | 22.2 mg |
| NaCl | 0.8% | 800 mg |
| MgSO$_4$ | 2 mM | 49 mg |
| (VITC) | 4 mM | 70 mg |
| Glucose | 0.6 mM | 100 mg |
| HEPES | 25 mM | 595 mg |
| Tris | 10 mM | 120 mg |
| NaHCO$_3$ | 4.2 mM | 34.5 mg |
| KH$_2$PO$_4$ | 1.25 mM | 17 mg |
| ⇓ | | |
| 100 ml H$_2$O | | |
| MEM medium 1× | | |
| MEM 2× | 25 ml | |
| Tris | 60 mg | |
| NaHCO$_3$ | 460 µl of 7.5% stock solution | |
| Penstrep | 1 ml | |
| ⇓ | | |
| 25 ml H$_2$O | the total made 50 ml | |
| ODM medium | | |
| MEM medium 1× | 50 ml | |
| Complementary medium | 50 ml | |
| ⇓ | | |
| Filter | | |
| pH 7.32 (before incubation) | | |
| pH 7.1 (after incubation) | | |
| | Osm 307 mosm/kg | |

We claim:

1. Device for studying and recording the electrophysiological phenomena in cultures of excitable tissues, said device comprising a combination of a lower half card comprising a perfusion medium in a perfusion chamber sealed by a permeable and transparent membrane and an upper half card with a flexible printed circuit bearing a network of electrodes and fitted with a cap for insuring the closure of the device.

2. The device of claim 1 wherein the card is made of two half-cards, the upper part and the lower part respectively fitted together to form an interface.

3. The device of claim 1 wherein it is made of a card constituting an electronic/biological interface which is intended to be inserted into an electronic module.

4. The device of claim 1 wherein the lower part of the card is made of plastic material and contains a cavity having an inlet and an outlet, and is delimited by a permeable and transparent membrane.

5. The device of claim 1 wherein the upper part of the card is fixed to the lower part by clips or screws.

6. The device of claim 1 wherein the upper part of the card is formed by a rigid element made of plastic material and a flexible printed circuit which forms a network of electrodes attached to connectors.

7. The device of claim 6 wherein a well in the rigid plastic material of the card contains a moveable sleeve which can progressively move downwards when a cap is screwed on said well.

8. The device of claim 1 wherein a flexible or rigid seal is placed between the two half-cards, to provide the permeability of a thus formed gaseous chamber.

9. The device of claim 1 wherein the permeable and transparent membrane is fixed on the lower part of the device on which tissue slices rest.

10. The device of claim 9 wherein the tissue slices are perfused in a continuous or discontinuous manner by a liquid nutrient.

11. The device of claim 1 wherein the card is perfused in a sterile manner with a medium for testing substances or mediators.

12. The device of claim 1 wherein the perfusion medium is selected from the group consisting of a control culture medium and an electrophysiological medium.

13. The device of claim 1 wherein the perfusion medium is a selected culture medium.

14. A method comprising simultaneously measuring and recording electrophysiological phenomena of excitable cells using a device of claim 1.

15. A method of claim 14 wherein the device is utilized for said measuring and recording of the electrophysiological activity of cultures of cells and performing biochemical analysis.

16. A method of claim 14 wherein the device is utilized for the simultaneous recording of electrophysiological activity and biochemical analysis of a microdyalisate after stimulation of the nervous system.

17. A method of claim 14 in which the device is utilized for the simultaneous recording of electrophysiological activity of neuronal cells and biological analysis of an hippocampal slice culture of a neuro-active substance, after stimulation.

18. A method according to claim 17 wherein the neuro-active substance is a mediator.

* * * * *